United States Patent

Tahara et al.

[11] Patent Number: 4,546,107
[45] Date of Patent: Oct. 8, 1985

[54] 1,4-METHANO-2-BENZAZEPINE DERIVATIVES USEFUL AS CEREBAL DYSFUNCTION-IMPROVING DRUGS, ANTI-CONVULSANT, ANTI-EPILEPTIC OR ANTI-ANXIETY DRUGS

[75] Inventors: Tetsuya Tahara, Nakatsu; Masafumi Arita, Tokyo; Tsuyoshi Kuroda, Nakatsu, all of Japan

[73] Assignee: Yoshitomi Pharmaceutical Industries, Ltd., Osaka, Japan

[21] Appl. No.: 609,866

[22] PCT Filed: Aug. 30, 1983

[86] PCT No.: PCT/JP83/00286

§ 371 Date: May 7, 1984

§ 102(e) Date: May 7, 1984

[87] PCT Pub. No.: WO84/00961

PCT Pub. Date: Mar. 15, 1984

[30] Foreign Application Priority Data

Sep. 7, 1982 [JP] Japan ................................ 57-155584
Sep. 7, 1982 [JP] Japan ................................ 57-155585

[51] Int. Cl.⁴ .................... A61K 31/40; C07D 207/56
[52] U.S. Cl. .................... 514/411; 548/427
[58] Field of Search .................... 548/427; 424/274

[56] References Cited

U.S. PATENT DOCUMENTS 3,474,463 10/1969 Schenker ............................ 548/434
3,890,347 6/1975 Middlemiss ........................ 548/427

FOREIGN PATENT DOCUMENTS 4322097 9/1968 Japan .
7216762 6/1973 Netherlands ........................ 548/427
1401287 7/1975 United Kingdom ................ 548/427

OTHER PUBLICATIONS

Middlemiss, Chem. Abst., vol. 79 (1973) 66171u.
CIBA Ltd., Chem. Abst., vol. 65, 696f.
Faculty of Pharmaceutical Science, Chem. Pharm. Bull. 14(4) 324–329 (1966).
Tadashi Kometani et al., J. M. Chem. 1978, vol. 21, No. 11, 1105–1110.

Primary Examiner—Donald G. Daus
Assistant Examiner—Cecilia Shen
Attorney, Agent, or Firm—Wenderoth, Lind & Ponack

[57] ABSTRACT

1,4-Methano-2,3,4,5-tetrahydro-1H-2-benzazepin-3-one derivatives of the formula:

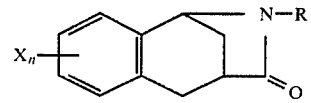

wherein X is halogen, n is 1 or 2, and R is hydrogen, lower alkyl or phenyl-lower alkyl. They are useful as medicaments, e.g. cerebral dysfunction-improving drugs, anti-convulsants, anti-epileptics and anti-anxiety drugs.

10 Claims, No Drawings

1,4-METHANO-2-BENZAZEPINE DERIVATIVES USEFUL AS CEREBAL DYSFUNCTION-IMPROVING DRUGS, ANTI-CONVULSANT, ANTI-EPILEPTIC OR ANTI-ANXIETY DRUGS

TECHNICAL FIELD AND DISCLOSURE OF INVENTION

This invention relates to novel and therapeutically useful 1,4-methano-2,3,4,5-tetrahydro-1H-2-benzazepin-3-one derivatives represented by the formula:

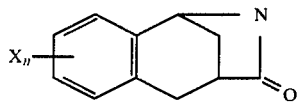

(I)

wherein X is halogen (fluorine, chlorine, bromine or iodine), n is 1 or 2 and R is hydrogen, lower alkyl (methyl, ethyl, propyl, isopropyl, butyl, etc.) or phenyl-lower alkyl (benzyl, phenethyl, etc.).

Japanese Patent Publication No. 43-22097 (1968), Chem. Pharm. Bull., 14, 324 (1966) and J. Med. Chem., 21, 1105 (1978) mention compounds of the formula:

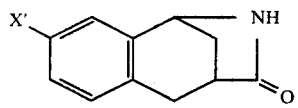

wherein X' is hydrogen or methoxy, which compounds are useful as an intermediate for the synthesis of certain analgesics.

The present inventors have synthesized various compounds having a moiety of 5-membered ring lactam formed by intramolecular ring-closure of gamma-aminobutyric acid (hereinafter abbreviated as GABA) in their structure to investigate their utility. As a result, it has been found that the compounds of the invention have potent antagonistic activities against lethality and convulsions induced by GABA antagonist such as picrotoxin or bicuculline and accordingly, GABA-like activities. GABA per se is considered to be difficult to transmit blood-brain barrier when administered peripherally, so that effects on the central nervous system can be little expected. On the contrary, the compounds of the invention have the aforementioned effects even when orally administered and so are highly useful.

Further, the compounds of the invention have antielectroshock and antimetrazole actions or electrocorticogram-improving action in a temporary cerebral ischemia model, antihypoxia action and the like. Thus, they are also useful as drugs for improving cerebral dysfunction, anticovulsants, antiepileptics, antianxiety drugs, or other medicaments.

On the other hand, the known compounds mentioned above are extremely weak in such actions as compared with the compounds of the invention or practically ineffective in such actions.

The compounds of Formula (I) can be produced by subjecting an oxime compound of the formula:

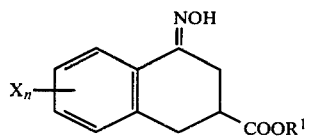

(II)

to reducing followed by ring-closure of the resulting product, wherein X and n are the same as defined above, and $R^1$ is hydrogen or lower alkyl.

The reaction is preferably catalytic reduction, which is carried out in the presence of a metallic catalyst such as Reney nickel, platinum oxide or palladium carbon, in an inert solvent preferably lower alkanol such as methanol or ethanol or lower alkanoic acid such as acetic acid, if desired in the presence of ammonia for the prevention of possible polymerization, at a temperature of from room temperature to 150° C, preferably 50° to 100° C., under an ordinary pressure or 50 to 150 atm of hydrogen. Hydrogen or hydrazine may be used as a source of hydrogen. The reduction can also be carried out by the use of sodium in liquid ammonia containing methanol or by the use of a metal such as zinc or tin and an acid such as hydrochloric acid or acetic acid.

Where the reaction is carried out over about 60° C., there can be obtained the objective compounds of the formula:

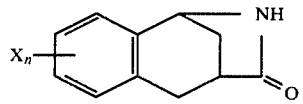

(Ia)

wherein X and n are the same as defined above, without isolating the intermediate of the formula:

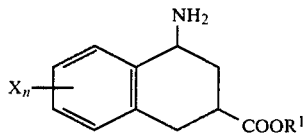

(III)

wherein X, n and $R^1$ are the same as defined above.

Otherwise, the intermediate can be isolated and then converted into the compound (Ia) by heating at 60°–200° C.

The compound of Formula (III) in trans-form does not participate in the ring-closure reaction, but can be separated by extraction with an acid or alkali.

The compound of Formula (Ia) is allowed to react with an alkylating agent such as dimethyl sulfate, diethyl sulfate or a compound of the formula:

$R^2$—Y  (IV)

wherein $R^2$ is lower alkyl or phenyl-lower alkyl, and Y is a reactive residue such as halogen, methylsulfonyloxy or p-tolylsulfonyloxy, to give the objective products of the formula:

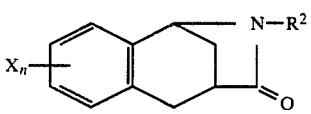

(Ib)

wherein X, n and $R^2$ are the same as defined above.

The reaction is carried out by treating the compound (Ia) with an alkali metal compound such as lithium hydride, sodium hydride, potassium hydride, sodium amide, diisopropylaminolithium, sodium methoxide or sodium ethoxide, in an inert solvent such as benzene, toluene, tetrahydrofuran, dioxane, dimethylformamide or dimethyl sulfoxide, then with an alkylating agent, usually at 0° C. to the refluxing temperature of the solvent for several hours.

The compounds of Formula (I) can also be prepared by subjecting a compound of the formula:

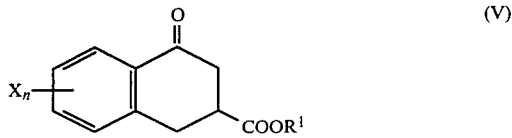

to catalytic reduction, wherein X, n and $R^1$ are the same as defined above, in the coexistence of an amine of the formula:

R—NH$_2$      (VI)

wherein R is the same as defined above, if necessary followed by ring-closure under heating.

The pharmacological properties of the compounds of the invention are shown below.

Test Method

1. Anti-picrotoxin Action

Groups each of 7–14 male dd mice were used. A test compound was orally administered and 60 minutes thereafter, picrotoxin (5 mg/kg) was administered subcutaneously. The 50% anti-lethal dose (ED$_{50}$) was calculated from the servival rate within 30 minutes.

2. Anti-bicuculline Action

Groups each of 4–14 male dd mice were used. Each test compound was administered orally and 60 minutes thereafter, bicuculline (0.6 mg/kg) was administered intravenously. The dose (ED$_{50}$) required for 50% suppression of the occurrence of tonic-extensile convulsions within 5 minutes against the control group was determined.

| Test Compound | Results Anti-picrotoxin-lethal action, ED$_{50}$ mg/kg, p.o. | Anti-bicuculline-convulsive action, ED$_{50}$ mg/kg, p.o. |
|---|---|---|
| A | 62 | 95 |
| B | 66 | 45 |
| C | 50 | 73 |
| D(Comparison) | 1100 | >1000 |
| E(Comparison) | >100 (0%) | >100 (0%) |

A: Compound of Example 1
B: Compound of Example 2
C: Compound of Example 3
D: 1,4-Methano-2,3,4,5-tetrahydro-1H—2-benzazepin-3-one (known compound)
E: 8-Methoxy-2-methyl-1,4-methano-2,3,4,5-tetrahydro-1H—2-benzazepin-3-one (known compound)

The compounds of Formula (I) of the invention, when used as medicines, can be administered orally or parenterally in the form of pharmaceutical agent in combination with a pharmaceutically acceptable and suitable carrier. The pharmaceutical agent may take any conventional form such as tablets, capsules, granules, powders, injectable solutions, etc. The daily dose for human adults usually ranges from about 10 mg to about 500 mg for oral administration, in single or multiple doses, but the dosage may vary depending upon the age, the weight and/or the conditions of a patient to be treated and the response to the medication.

The invention will be explained more concretely by the following examples, but they are not to be construed as limiting the present invention.

EXAMPLE 1

A solution of 80 g of methyl 6 -chloro-4-hydroxyimino-1,2,3,4-tetrahydro-2-naphthoate in a mixture of 1 liter of methanol and 100 ml of 10% ammonia-methanol is placed in an autoclave and 10 g of Raney nickel catalyst is added. An initial hydrogen pressure of 60 atm is applied, and the catalytic reduction is carried out at 60°–70° C. for 3 hours. After the reactant is allowed to cool, the catalyst is filtered off, the filtrate is concentrated, and the residual oil is extracted with chloroform. The chloroform layer is washed with aqueous potassium carbonate solution followed by water and dried over sodium sulfate, and the chloroform is distilled off. The residue is heated at 120° C. on an oil bath for 2 hours and then dissolved in chloroform. The solution is washed with 5% hydrochloric acid and dried over sodium sulfate, and the solvent is distilled off. The residual solid is recrystallized from a mixture of ether and acetone to give 25 g of 8-chloro-1,4-methano-2,3,4,5-tetrahydro-1H-2-benzazepin-3-one, m.p. 212°–215° C., in the form of colorless crystals.

EXAMPLE 2

To a solution of 2 g of 8-chloro-1,4-methano-2,3,4,5-tetrahydro-1H-2-benzazepin-3-one in 15 ml of dimethylformamide is added gradually 1 g of 50% sodium hydride (in mineral oil) under ice-cooling. The mixture is then stirred at 40°–50° C. for 1 hour. It is again cooled in an ice-bath, and 3 g of methyl iodide is added dropwise. The reactant solution is then stirred at room temperature for 3 hours. The reaction mixture is poured into icecold water, neutralized with dilute hydrochloric acid, and extracted with ethyl acetate. The organic layer is washed with water and dried, and the solvent is distilled off. When the residual oil is treated with hexane, crystallization takes place. The crystalline product thus obtained is collected by filtration and recrystallized from a mixture of isopropyl ether and hexane to give 1.5 g of 8-chloro-2-methyl-1,4-methano-2,3,4,5-tetrahydro-1H-2-benzazepin-3-one, m.p. 88°–91° C., in the form of colorless crystals.

EXAMPLE 3

A solution of 14.4 g of methyl 5,7-dichloro-4-hydroxyimino-1,2,3,4-tetrahydro-2-naphthoate in a mixture of 80 ml of acetic acid and 100 ml of methanol is charged in an autoclave. Platinum oxide catalyst, 0.8 g, is added and reduction is carried out under an initial hydrogen pressure of 40 atm and 40°–50° C. for 7 hours. After the reactant is allowed to cool, the catalyst is filtered off, and the filtrate is concentrated under reduced pressure. The residual oil is dissolved in chloroform. The solution is washed with aqueous potassium carbonate solution followed by water and dried over sodium sulfate, and the chloroform is distilled off. The residual semi-solid is heated at 110°–120° C. on an oil bath for 2 hours and then cooled. The resulting product is crystallized with ethyl acetate. The crystalline product thus obtained is collected by suction filtration and recrystallized from a mixture of ethyl acetate and ethanol to give 4.7 g of 6,8-dichloro-1,4-methano-2,3,4,5-tetrahydro-1H-2-benzazepin-3-one, m.p. 186°–188° C., in the form of colorless crystals.

The following compounds are produced in the same procedure as the above Examples.

4. 6-Chloro-1,4-methano-2,3,4,5-tetrahydro-1H-2-benzazepin-3-one, m.p. 187°–189° C.
5. 6-Chloro-2-methyl-1,4-methano-2,3,4,5-tetrahydro-1H-2-benzazepin-3-one, m.p. 137°–139° C.
6. 7-Chloro-1,4-methano-2,3,4,5-tetrahydro-1H-2-benzazepin-3-one, m.p. 120°–123° C.
7. 2-Butyl-8-chloro-1,4-methano-2,3,4,5-tetrahydro-1H-2-benzazepin-3-one, m.p. 75°–77° C.
8. 8-Chloro-2-phenethyl-1,4-methano-2,3,4,5-tetrahydro-1H-2-benzazepin-3-one, m.p. 113°–115° C.
9. 8-Fluoro-1,4-methano-2,3,4,5-tetrahydro-1H-2-benzazepin-3-one, m.p. 203°–205° C.
10. 8-Fluoro-2-methyl-1,4-methano-2,3,4,5-tetrahydro-1H-2-benzazepin-3-one, m.p. 120°–123° C.
11. 6,7-Dichloro-1,4-methano-2,3,4,5-tetrahydro-1H-2-benzazepin-3-one, m.p. 196°–200° C.
12. 6,7-Dichloro-2-methyl-1,4-methano-2,3,4,5-tetrahydro-1H-2-benzazepin-3-one, m.p. 148°–150° C.
13. 7,8-Dichloro-1,4-methano-2,3,4,5-tetrahydro-1H-2-benzazepin-3-one, m.p. 215°–217° C.
14. 7,8-Dichloro-2-methyl-1,4-methano-2,3,4,5-tetrahydro-1H-2-benzazepin-3-one, m.p. 134°–136° C.
15. 8-Bromo-1,4-methano-2,3,4,5-tetrahydro-1H-2-benzazepin-3-one.

The invention has been disclosed fully in the description given above including Examples, but various alterations and modifications can be made without departing from the spirit and scope of the invention.

We claim:
1. 1,4-Methano-2,3,4,5-tetrahydro-1H-2-benzazepin-3-one compounds represented by the formula:

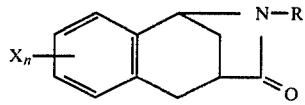

wherein X is halogen, n is 1 or 2, and R is hydrogen, lower alkyl or phenyl-lower alkyl.

2. A compound of claim 1: 8-chloro-1,4-methano-2,3,4,5-tetrahydro-1H-2-benzazepin-3-one.
3. A compound of claim 1: 8-chloro-2-methyl-1,4-methano-2,3,4,5-tetrahydro-1H-2-benzazepin-3-one.
4. A compound of claim 1: 6,8-dichloro-1,4-methano-2,3,4,5-tetrahydro-1H-2-benzazepin-3-one.
5. A compound of claim 1: 6-chloro-1,4-methano-2,3,4,5-tetrahydro-1H-2-benzazepin-3-one.
6. A compound of claim 1: 6-chloro-2-methyl-1,4-methano-2,3,4,5-tetrahydro-1H-2-benzazepin-3-one.
7. A compound of claim 1: 7-chloro-1,4-methano-2,3,4,5-tetrahydro-1H-2-benzazepin-3-one.
8. A compound of claim 1: 8-fluoro-1,4-methano-2,3,4,5-tetrahydro-1H-2-benzazepin-3-one.
9. A compound of claim 1: 8-fluoro-2-methyl-1,4-methano-2,3,4,5-tetrahydro-1H-2-benzazepin-3-one.
10. A cerebal dysfunction-improving, anti-convulsant, anti-epileptic or anti-anxiety composition comprising a effective amount of said compound of claim 1 and a pharmaceutically acceptable carrier.

* * * * *